US008768441B2

(12) United States Patent
De Zwart et al.

(10) Patent No.: US 8,768,441 B2
(45) Date of Patent: Jul. 1, 2014

(54) TIME COORDINATION AND SYNCHRONIZATION OF EVENT TIMES IN ELECTRONIC MEDICAL RECORDS

(75) Inventors: Aga De Zwart, Boulder, CO (US); Donald R. Boucher, Andover, MN (US); David G. Cohen, Boulder, CO (US); Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1944 days.

(21) Appl. No.: 10/969,765

(22) Filed: Oct. 20, 2004

(65) Prior Publication Data

US 2005/0192846 A1 Sep. 1, 2005

Related U.S. Application Data

(60) Provisional application No. 60/512,883, filed on Oct. 20, 2003.

(51) Int. Cl.
*A61N 1/08* (2006.01)
*A61N 1/362* (2006.01)

(52) U.S. Cl.
CPC .................................... *A61N 1/3625* (2013.01)
USPC .......................................................... 600/510

(58) Field of Classification Search
CPC . A61N 1/3711; A61N 1/3625; A61B 5/0006; H04J 3/0652
USPC ......... 600/373, 382, 374, 384, 508, 509, 510; 607/4, 5, 9, 116
See application file for complete search history.

(56) References Cited

U.S. PATENT DOCUMENTS 4,945,477 A 7/1990 Edwards
5,549,115 A 8/1996 Morgan et al.
5,778,882 A 7/1998 Raymond et al.
5,784,421 A * 7/1998 Dolev et al. .................. 375/354
5,785,043 A * 7/1998 Cyrus et al. .................. 600/525
5,860,918 A 1/1999 Schradi et al.
5,891,046 A 4/1999 Cyrus et al.
5,921,938 A 7/1999 Aoyama et al.
5,951,485 A * 9/1999 Cyrus et al. .................. 600/523
6,095,985 A 8/2000 Raymond et al.
6,216,096 B1 4/2001 Obermeier
6,282,441 B1 8/2001 Raymond et al.
6,542,910 B2 4/2003 Cork et al.
7,124,190 B1 * 10/2006 Moore .......................... 709/229
2003/0065536 A1 4/2003 Hansen et al.
2004/0172070 A1 9/2004 Moore et al.

* cited by examiner

*Primary Examiner* — Christopher D Koharski
*Assistant Examiner* — Frances Oropeza
(74) *Attorney, Agent, or Firm* — Fish & Richardson P.C.

(57) ABSTRACT

A computer-implemented method of recording the times of events related to the medical care delivered to patient, and for integrating those times to provide a patient history, including recording a first time of occurrence of a first event, recording first clock information characterizing a first time source from which the first time of occurrence was obtained, recording a second time of occurrence of a second event, recording second clock information characterizing a second time source from which the second time of occurrence was obtained, wherein the first time source and the second time source are independent of one another and not synchronized with one another, transferring recorded data so that the first time of occurrence, first clock information, second time of occurrence, and second clock information are accessible at a computer; and producing a patient history using at least the first and second times of occurrence.

7 Claims, 5 Drawing Sheets

| Device ID | Device Type | Call Time | Dispatch Time | Time on Scene | Defib Turn on | Defib Shock #1 | Defib Shock #n | Therapy #1 | Therapy #n | Diagnostic #1 | Diagnostic #n | Arrive at Hospital |
|---|---|---|---|---|---|---|---|---|---|---|---|---|
| 4323554 | CAD | 08:43:34 | 08:45:03 | 08:49:54 | | | | | | | | |
| 8735790 | Defib | | | | 08:51:11 | 08:51:11 | 08:55:21 | xx:xx:xx | xx:xx:xx | xx:xx:xx | xx:xx:xx | xx:xx:xx |
| 5389042 | RRPC | | | yy:yy:yy | yy:yy:yy | yy:yy:yy | yy:yy:yy | yy:yy:yy | yy:yy:yy | yy:yy:yy | yy:yy:yy | yy:yy:yy |
| 5794258 | PhysMon | | | | | | | | | zz:zz:zz | zz:zz:zz | |

| Field | Field Number | Type | Comments |
|---|---|---|---|
| Device_ID | 1 | Long | Unique ID of record |
| Clock_Date | 2 | Date | The start date of the code from the point of view of the clock |
| Clock_Time | 3 | Time | The start time of the code from the point of view of the clock |
| Clock_ID | 4 | Integer | ID of the clock (1=external #1, 2=external #2, 3=page system, 4=codewrite, 5=defib, 6=sync station, 7=LAN, 8=atomic clock) |
| Time_Source Quality | 5 | Date/Time | Accuracy of clock in minutes per month |
| Last_Synchronization | 6 | Date/Time | Date and time of last time synchronization |
| Drift | 7 | Date/Time | Amount of error calculated at last time synchronization |
| Drift Synchronization Reference Source | 8 | Integer | ID of the clock (1=external #1, 2=external #2, 3=page system, 4=codewrite, 5=defib, 6=sync station, 7=LAN, 8=atomic clock) |

FIG. 3

| | A | B | C | D |
|---|---|---|---|---|
| A | — | +X | | |
| B | -X | — | +Y | |
| C | | -Y | — | |
| D | | | | — |

FIG. 4

| Field | Field Number | Type | Comments |
|---|---|---|---|
| Record_ID | 1 | Long | Unique ID of record |
| Clock_Start_Date | 2 | Date | The start date of the code from the point of view of the clock |
| Clock_Start_Time | 3 | Time | The start time of the code from the point of view of the clock |
| Clock_ID | 4 | Integer | ID of the clock (1=external #1, 2=external #2, 3=page system, 4=codwrite, 5=defib, 6=sync station, 7=LAN, 8=atomic clock) |
| External_1_Delta | 5 | Time Delta (hhhhh:mm:ss) | Delta from external delta 2, Commonly "clock on wall" in room where code occurs |
| External_Base_Time_1_Descr | 6 | String(100) | Description of base time 1 reference clock |
| External_2_Delta | 7 | Time Delta (hhhhh:mm:ss) | Delta from external delta 2, typically scribe's wristwatch |
| External_Base_Time_2_Descr | 8 | String(100) | Description of base time 2 reference clock |
| Page_System_Delta | 9 | Time Delta (hhhhh:mm:ss) | Delta from Paging system |
| CodeWrite_Delta | 10 | Time Delta (hhhhh:mm:ss) | Delta from CodeWrite PDA |
| Defib_Delta | 11 | Time Delta (hhhhh:mm:ss) | Delta from Defib |
| Sync_Station_Delta | 12 | Time Delta (hhhhh:mm:ss) | Delta from station performing synchronization (data moving to LAN from PDA) |
| LAN_Delta | 13 | Time Delta (hhhhh:mm:ss) | Delta from local area network |
| Atomic_Delta | 14 | Time Delta (hhhhh:mm:ss) | Delta from atomic clock |
| Other data.... | | | |

FIG. 5

TIME COORDINATION AND SYNCHRONIZATION OF EVENT TIMES IN ELECTRONIC MEDICAL RECORDS

CROSS-REFERENCE TO RELATED APPLICATION

This application claims priority to U.S. Provisional Application Ser. No. 60/512,883, filed on Oct. 20, 2003.

TECHNICAL FIELD

This invention relates to recording and later synchronizing event times recorded on medical devices.

BACKGROUND

Emergency medical care delivered to a patient occurs primarily in one of two settings: in hospitals by nurses and physicians, and in the field by trained emergency service providers, typically in the form of police officers, emergency medical technicians (EMTs), fire departments, paramedics or physicians in some cases. In the best medical systems, programs are put into place to assess current levels of care and to provide continuous quality-of-care improvements. Common measures of system effectiveness are endpoints such as survival, in the case of cardiac arrest, or improvement in health, in the case of non-terminal events. Additional interim measures are also important, however in determining areas for improvement in care; these data include response time and protocol adherence. While electronic patient charting software is now available, it is not uncommon to still see paper run reports being generated by emergency health care providers to record a patient's relevant personal information as well as the specifics of the vital signs of the patient and treatments delivered to the patient. The so-called run report or patient chart (RRPC) can subsequently be used by medical supervisory persons such as the Medical Director to determine statistical summaries of medical care performance. A common reporting format for care and outcomes, particularly in the pre-hospital setting, is the Utstein Style format as promulgated by the American Heart Association and other organizations. It is often the case that computers are used to enter data from paper run reports, the subsequent digital data then being processed to determine the aforementioned outcome and quality of care statistics as well as paper and electronic reports.

Data important to the determination of system effectiveness within the context, for instance, of treatment of cardiac arrest are critical time durations such as: time from 911 emergency phone call to arrival of the ambulance at the scene, time duration of transport from the scene to the hospital, time from arrival at the scene to delivery of the various medical therapies. The calculation of these durations involves multiple clock sources resident in the various diagnostic and therapeutic medical devices, the portable computer-based RRPC devices and the hospital and medical center-based base station computers.

Prior art has recognized the need for synchronization of more than one record stream to produce one integrated treatment history. E.g., U.S. Pat. Nos. 5,778,882, 6,095,985 and 6,282,441 provide for time-correlated medical event data on a personal digital assistant (PDA). Synchronization is performed based on time stamps for each record generated in the particular device; as a result, synchronization depends on how well the different clocks on the different devices are synchronized. U.S. Pat. Nos. 5,549,115 and 5,785,043 achieve an improvement in synchronization accuracy by storing the time-stamped event data in a removable memory device that has a built-in clock where the event times are correlated to the medical device clock time and the correlation is stored onto the memory device. When the data is downloaded from the memory device by an instrument such as a PDA or computer, the clock time as well as the correlation value are retrieved and when compared with the current time of the PDA clock, the record streams can be synchronized. U.S. Pat. No. 5,951,485 is very similar to U.S. Pat. No. 5,778,882 with the exception that it provides for more accurate time synchronization by communicating the current time of the device on which the data is stored to the PDA, which then determines a differential time discrepancy. The calculated time differential is used to more accurately correlate the events of the two devices.

SUMMARY

In general the invention features a computer-implemented method of recording the times of events related to the medical care delivered to patient, and for integrating those times to provide a patient history. The method comprises recording a first time of occurrence of a first event, recording first clock information characterizing a first time source from which the first time of occurrence was obtained, recording a second time of occurrence of a second event, recording second clock information characterizing a second time source from which the second time of occurrence was obtained, wherein the first time source and the second time source are independent of one another and not synchronized with one another, transferring recorded data so that the first time of occurrence, first clock information, second time of occurrence, and second clock information are accessible at a computer; and producing a patient history using at least the first and second times of occurrence.

Preferred implementations of the invention may incorporate one or more of the following: The first time of occurrence and first clock information may be recorded on a first device, and wherein the second time of occurrence and second clock information may be recorded on a second device, which is different from the first device. The method may further comprise selecting one of the first and second time sources as a reference time source, synchronizing the first and second times of occurrence to the reference time source, and producing a patient history in which times of occurrence of events are expressed relative to the reference time source. The method may further comprise revising the selection of the reference time source to select a different one of the first and second time sources as a revised reference time source, and producing a revised patient history in which times of occurrence of events are expressed relative to the revised reference time source. Further events may be recorded, and for each event there may be recorded a time of occurrence and clock information characterizing the time source from which the time of occurrence was obtained. The information characterizing the time source may comprise the identity of the time source. There may be a plurality of known time sources. The information characterizing the time source may comprise information characterizing the quality of the time source. The information characterizing the time source may comprises information regarding the length of time since the time source was last synchronized with an accurate reference clock. The information characterizing the time source may comprise information regarding the drift of the time source. The drift may be calculated by measuring the time error relative to an accurate reference clock after an extended period of time. The patient history may comprise an integrated electronic patient record. The first device may be a defibrillator, a personal digital assistant, a Tablet PC, a laptop computer, a physiological monitoring device, or similar device, and the second device may be a different defibrillator, personal digital assistance, Tablet PC, laptop computer or physiological monitoring device. The transferring of recorded data may comprise transferring a file from the first device to another device over a network.

In preferred implementations, all or part of the absolute time information is maintained subsequent to the integration of more than one record. This permits time aligning of the records to be varied during the review process following the event.

This invention can be used in any system that records information relevant to a medical procedure from multiple independent sources such as medical devices (physiological monitoring, defibrillators, etc.), portable electronic devices such as a personal digital assistant (PDA), Tablet PC, laptop or other such device that is used to record electronically treatments delivered to a patient as well as actual protocols followed during a medical procedure and medical events and data arising from the medical or physiological condition of the patient.

Among the many advantages of the invention (some of which may be achieved only in some of its various aspects and implementations) are that the invention can achieve synchronization accuracy without a master clock, and without requiring that a memory device and clock communicate directly with the device to which the data is to be downloaded. Accurate synchronization of multiple electronic records can be achieved even when one or more of the records is transferred as a file by such means as electronic mail (email) via a distributed environment like the Internet.

With the invention, information flow need not be unidirectional, i.e., it need not flow from the individual devices up to some centralized data management and viewing location, typically a computer with specialized software in a medical director's office or in the emergency system's central dispatch location. Unidirectional data flow has limited the ability of personnel to access and derive the benefits from the information in the integrated electronic record. With the invention there can be multidirectional information flow, enabling multiple users in locations remote from central dispatch to recreate an accurate sequence of events.

The invention overcomes limitations of the prior art with regard to synchronizing multiple electronic records in a distributed environment. Information characterizing the time source from which a time of occurrence is obtained is stored along with the event data.

BRIEF DESCRIPTION OF THE DRAWINGS

FIG. 3 is a table providing the data structure of an individual device record within the time base quality information record.

FIG. 4 is a representation of a sparsely-filled, 4×4 Δ-matrix.

FIG. 5 is an IEPR for a hospital cardiac arrest incident.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

The descriptions below are more than sufficient for one skilled in the art to construct the disclosed implementations. Unless otherwise mentioned, the processes and manufacturing methods referred to are ones known by those working in the art.

Figure 1:
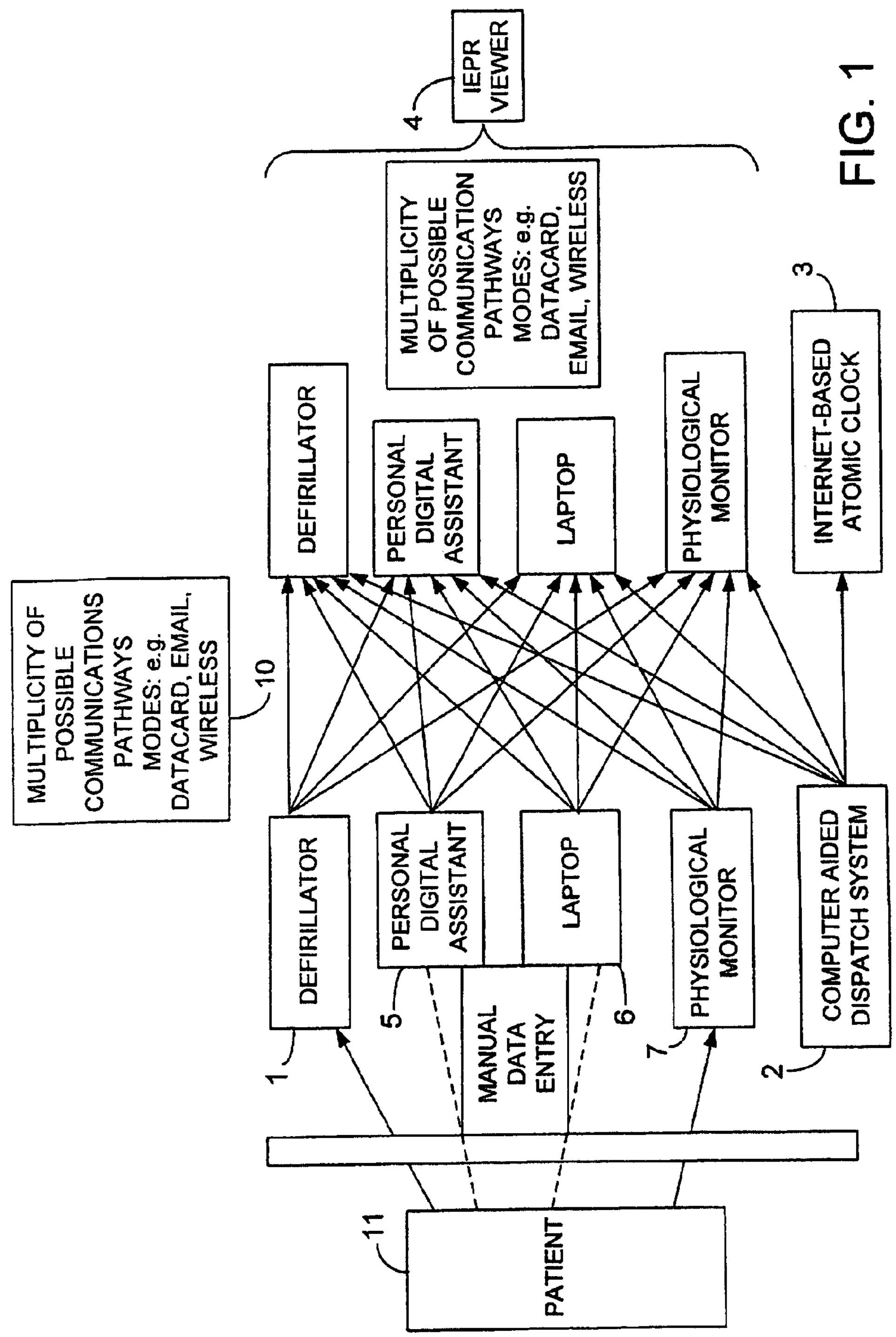
FIG. 1 is a block diagram of a system with a defibrillator, an RRPC, a dispatch system and other participating devices.
Figure 2:
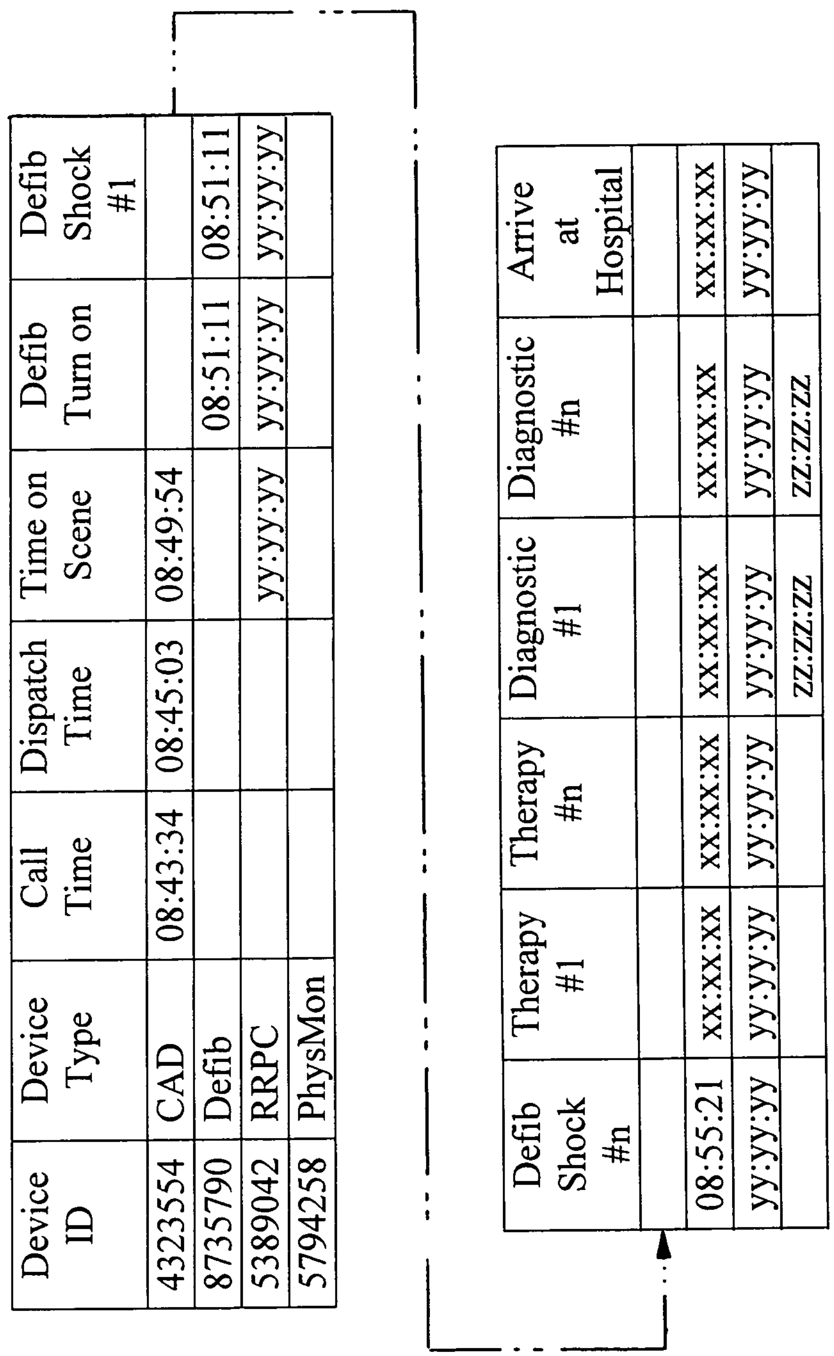
FIG. 2 is a table providing the data structure of the database of the integrated electronic patient record of one implementation of the invention.

Referring to FIG. 1, the diagram visually describes what might be encountered in the pre-hospital environment during a cardiac arrest. A similar diagram can be presented for the cardiac arrest in the hospital environment or other specific medical event. In the case of the pre-hospital cardiac arrest, when a bystander witnesses a cardiac arrest, they will call 911. A computer aided dispatch system (CAD) 2 receives the call and dispatches an appropriate emergency crew to the scene. Referring to FIG. 2, the Call Time, Dispatch Time, and Time on Scene are recorded in the CAD 2 database. A paramedic crew will sometimes have a second rescuer whose responsibility is to log specific events into the PDA. In the preferred embodiment, RRPC software is used (manufactured by ZOLL Data Systems of Boulder, Colo. called RescueNet Code Review. Software may also be available for use on a laptop computer 6, similar in functionality to the Rescue Net Code Review). When the ambulance arrives on scene, a paramedic will record on the PDA 5 the Time on Scene and subsequent times such as Defib Turn On. The patient 11 is treated by the paramedic with the defibrillator 1, which records a variety of digital information in non-volatile memory, often in the form of removable datacards. During the course of the treatment of the patient, the patient may be monitored by a physiological monitor 7. Physiological readings are recorded on the monitor 7 preferably in fixed or removable non-volatile memory.

Through the use of Bluetooth technology, it is now possible to sense physical proximity to other devices. Preferably, the defibrillator 1, PDA 5, and monitor 7 all incorporate Bluetooth wireless technology. The software in those devices can then automatically detect the presence of the other devices, identify themselves to each of the devices and share the current time with each other. This can be accomplished using Bluetooth "discovery" features defined by the Bluetooth special interest group standards.

Referring to FIG. 3, in some implementations of the invention, the clock information for each of the clocks characterizing the time source may identify the time source as one of a list of system-wide reference clocks, as shown in FIG. 3 with the Clock_ID field equal to 6 or 8. The clock information may also include means for specifying the particular reference clock used as the time base source. Clock information may also describe which device the time base was used for; for instance, the information might include device type such as a defibrillator, device manufacturer, e.g. ZOLL, serial number, and model number. The clock information may be in the form of codes or extended markup language (XML).

The clock information may include time base quality information (TBQI) that includes information regarding the length of time since the local clock was last synchronized with one of the reference clocks (Last_Synchronization in FIG. 3). TBQI may include information regarding the drift of the local clock (Drift in FIG. 3) as calculated by initially synchronizing the local clock to a reference clock then measuring the time error relative to a reference clock after an extended period of time such as a month.

It is not necessary that there be a master clock that acts as the absolute time reference. Time correlation of the multiple electronic records is an extended process with all time bases and their associated electronic record event sequences allowed to coexist and be displayed to the user. In some implementations, at least some portion of the structure of each multiple electronic record (MEP) is preserved in the integrated electronic patient record (IEPR) composed of those individual electronic records. As part of the process of viewing the IEPR, the individual events from each of the MEPs can be sorted and displayed to the user based on the time base information.

In other implementations, the particular source and quality of the time base determines which of the time bases will act as the reference clock. For instance, a defibrillator 1 in use in the field, such as the M-Series manufactured by ZOLL Medical Chelmsford, may have a built-in global positioning system (GPS) receiver providing the device with millisecond-level timing accuracy while the clock on the computer aided dispatch (CAD) system 2 or the medical director's computer 4 have been unable to synchronize with an Internet-based atomic clock 3 for an extended period of time and the normal drift of the computer clocks have introduced more error into these centralized 'master' clocks than is found on the field defibrillator. In such a case, the GPS-based time base would be used as the reference clock. The defibrillator, itself, may be able to provide better relative times related to the exact timing of a defibrillator shock than the PDA 5 or CAD 2 system; therefore in the case of relative timing of defibrillation shocks or other interventions, the defibrillator device or other interventional device may be used as the reference clock in the case of relative times of interventions delivered by that interventional device. The clock information shown on the display of the IEPR viewer may be a single time such as that of the GPS defibrillator clock along with an indication of the source for that clock. The clock information may also be shown as relative timing information such as the time from initial call into emergency services. The IEPR viewer user interface may include such features, known to those skilled in the art, as pull-down menus or pop-up menus to provide a list of all the time bases contained in the IEPR and the capability of manually selecting which time base will be used as a reference. Alternatively, the determination of which time base to use as the reference may be based on decision logic employed by the computer running the IEPR viewer software. That decision logic may be some simple deterministic IF-THEN-ELSE logic using the time base source and quality information, but given the fact that the uncertainties in time accuracies can be better modeled as probabilistic, decision techniques such as Bayesian methods and fuzzy logic are of benefit. One of the criteria in the decision-making logic may be what provides the least amount of uncertainty in the particular duration measures the user is attempting to make. Another criteria in the decision-making logic may be a user-entered value for the maximum desired error in time based calculations. This may take on the form of a list of maximum desired errors for particular durations (the value may not be the same for different durations). The user would be notified that the uncertainty had exceeded a maximum desired error threshold.

By maintaining the clock information along with the time of occurrence, relative time base information is not lost at the time of data download from one device to another. Maintaining that relative time base information as part of the IEPR has advantages. Referring to FIG. 4, the relative time base information can be stored in what can be termed a Δ-matrix, which provides, in a two-dimensional matrix, the relative offsets for each possible time source (time base) pair. Each cell in the matrix may be composed of a data object that includes the value of the relative offset as well as the determination method for that value. For instance, it may be that the relative offset was determined during the communications protocol between two devices during download of data as in the prior art. Alternatively, the relative offset may have been calculated during a calibration procedure performed automatically by the devices which would communicate, for instance via the Internet, with each other; in this instance, the determination method as well as when the calibration occurred would be included as part of the data object. Also included as part of the data object is an estimation of the accuracy of the relative offset. The initial form of the Δ-matrix will be sparsely populated, typically, but additional relative offsets can be calculated utilizing intermediate relative offsets. For instance, if the relative offset of time base 'A' to time base 'B', A−B+/−'X' milliseconds, is known, and the relative offset of time base 'B' to 'C', B−C+/−'Y' milliseconds is known, then relative offset A-C is likewise known. The error in such case is calculated as the root mean sum of squares (RMS).

Determination of relative offset information from electronic records transmitted by indirect means such as file-based methods like email or file transfer protocol (ftp) can be accomplished by first updating, if necessary, the relative offset of the file sending device to an accurate reference clock such as an Internet-based atomic clock and storing the offset into the electronic record. The file-receiving device may also update its relative offset to a reference clock as necessary. Then, using a method such as that incorporating the Δ-matrix, the relative offset can be calculated between the computers.

On the display of the IEPR viewer, visualization means may be provided for each displayed event time to indicate what the uncertainty is with that particular time. The uncertainty can be of the absolute accuracy of the time base or the relative accuracy of it with respect to another time base in the IEPR. The visualization can be in the form of error bars; multiple error bars can be presented for event, such as overlapping the bars and using such techniques as color-coding the bars. Color-coding of durations can be employed in reporting formats for care and outcomes, such as the Utstein Style format. For instance, colors can be used to indicate the potential accuracy of a particular duration, e.g., green to indicate highest accuracy, orange and red to indicate lesser degrees.

FIG. 5 is a table showing relevant parameters that could be determined during synchronization of the multiple clocks encountered during a medical event such as a "code" (cardiac incident) occurring in the hospital setting. In this situation, many of the devices are in close proximity, allowing for easier synchronization by such means as Bluetooth technology described earlier. There is a point in time when the code actually starts (Clock_Start_Time in FIG. 5). This is the earliest time at which the code was announced and is from the point of view of the clock used to announce the code. This may be the one time that is not local to the scene of the code, but may be a computer clock located at some central location from which a so-called "code team" is dispatched. A Code Team is the group of trained doctors and nurses designated for each shift to be on call in case of a cardiac arrest. The Clock_Start_Time may be a particularly important time in that it determines the calculation for the downtime, which typically is a very important measure with regard to analyzing the efficacy of the defibrillation therapy, as it establishes the length of time from a cardiac arrest until a defibrillation shock is delivered.

As was mentioned previously, through the use of Bluetooth technology, it is now possible to sense physical proximity to other devices. Preferably, the defibrillator 1, PDA 5, and monitor 7 all incorporate Bluetooth wireless technology. The software in those devices can then automatically detect the presence of the other devices, identify themselves to each of the devices and share the current time with each other. This can be accomplished using Bluetooth "discovery" features defined by the Bluetooth special interest group standards. When these devices are turned on at the time of a code, they will automatically synchronize with each other. In the prior art, one of the devices, such as the PDA became the reference device, and data was downloaded from the defibrillator and monitor at the end of the code into a single record; this scheme has the drawback that data download is a slow and cumbersome process that is not appropriate to have nurses or other caregivers perform. This may be avoided at least in some implementations of the invention, by each device calculating the relative time differences to each of the other devices to create a Δ-Matrix in each device. The data from each device may then be separately downloaded to a central computer containing the IEPR Viewer 4. Download may be accomplished by an ethernet connection or simply by removing a data storage card and carrying it to the IEPR Viewer 4. Because the Δ-Matrix is stored on each device including the datacard, this is now possible. In the situation where the Clock_Start_Time may be unknown to the various devices or clinical personnel at the time of the code (the code was called in to a remote central call location), the Clock_Start_Time may be transmitted from the centralized call computer to the IEPR Viewer computer 4 via such common means as the ethernet. One of the clocks listed in the Δ-Matrix will then be the IEPR Viewer computer clock and the centralised call center clock. As long as at least one of the data sources, e.g. the PDA, is actively synchronized with the IEPR computer 4, accurate relative times can be determined in order to provide an accurate measure of downtime.

In the implementation for the hospital cardiac arrest, each clock that is encountered throughout the code is synchronized using an algorithm that can calculate the difference between this clock and the "base clock" as the "clock delta". This is the difference, or "error" between the two clocks. Where possible, this clock delta is calculated by sampling the actual current time from each clock. In other cases, it is calculated by the use of an adjustment that requires user input. In these cases where no digital interface exists with the clock in question, the user is asked to enter the current time from the point of view of the external clock, thus providing a clock delta between it and the data entry device. This is best understood by example. Assume that there is a common wall clock in the room where the code is called. The clock delta cannot be captured directly, so the software asks the user for the current time from the point of view of the wall clock. The computing device asking this question presents the current time of the computing device, a time that is likely to be reasonably close to the time shown on the wall clock. The user is then given an easy way to adjust this time to what they see on the wall clock. By way of example, if the current time on the computing device is 13:05:27, and the user provides a current time for the wall clock of 13:04:05, then we can calculate the clock delta between the wall clock and the computing device as −00:01:22. Based on the type of clock encountered, the algorithm always arrives at a clock delta.

At some point, the user must enter the code start time and the clock used to record that time. Continuing with our example, if the code started at 12:31:00 from the point of view of the clock on the wall in the room, then the base clock start time is 12:31:00 and the base clock is the wall clock. This closely mimics the real world situation, in that any clock may be used to initially begin the code. This algorithm may be applied to any clock, but in any case we always arrive with a known base clock and a known base clock start time. This base clock start time is stored in the database (see FIG. 1, fields 2 and 3). The type of base clock is stored in this table as well (FIG. 1, field 4).

In FIG. 5, fields 5, 7, and 9-14 store the corresponding clock delta value.

Once the data arrives to the data review computer where the incident will be reviewed, the user can select any of the clocks that were encountered, and all times are adjusted to be from the point of view of the selected clock. This solves a very real world problem in that other paperwork or computing systems need only to have one clock in common (even if it is only the wall clock) and the user can see everything from the point of view of the other system. This is done by allowing the user to select the reference clock via an application menu. Based on the selected clock, all times are visually offset by the clock delta for that clock.

Many other implementations of the invention other than those described above are within the invention, which is defined by the following claims.

The invention claimed is:

1. A computer-implemented method of recording times of events related to the medical care delivered to patient, and for integrating those times to provide a patient history, the method being implemented using one or more non-transitory computer readable media, comprising:

recording a first time of occurrence of a first event;

recording first clock information characterizing a first time source from which the first time of occurrence was obtained;

recording a second time of occurrence of a second event;

recording second clock information characterizing a second time source from which the second time of occurrence was obtained, wherein the first time source and the second time source are independent of one another and not synchronized with one another;

transferring recorded data so that the first time of occurrence, the first clock information, the second time of occurrence, and the second clock information are accessible at a computer;

producing a patient history using at least the first and second times of occurrence, selecting one of the first and second time sources as a reference time source, synchronizing the first and second times of occurrence to the reference time source, and producing a patient history in which times of occurrence of events are expressed relative to the reference time source, wherein the patient history comprises an integrated electronic patient record.

2. The method of claim 1 wherein the first time of occurrence and the first clock information are recorded on a first device, and wherein the second time of occurrence and the second clock information are recorded on a second device, which is different from the first device.

3. The method of claim 1 wherein further events are recorded, and for each event there are recorded a time of occurrence and clock information characterizing a time source from which the time of occurrence was obtained.

4. The method of claim 1 wherein the time source has an identity and the information characterizing the time source comprises the identity of the time source.

5. The method of claim 4 wherein there are a plurality of known time sources.

6. The method of claim 1 wherein the time source has a quality and the information characterizing the time source comprises information characterizing the quality of the time source.

7. The method of claim 2 wherein the first device is selected from the group consisting of a defibrillator, a personal digital assistant, a Tablet PC, a laptop computer, and a physiological monitoring device, and the second device, different from the first device, is selected from the group consisting of a defibrillator, a personal digital assistance, a Tablet PC, a laptop computer and a physiological monitoring device.

* * * * *